United States Patent [19]
Yakuwa et al.

[11] Patent Number: 4,951,632
[45] Date of Patent: Aug. 28, 1990

[54] EXHAUST GAS COMPONENT CONCENTRATION SENSING DEVICE AND METHOD OF DETECTING FAILURE THEREOF

[75] Inventors: Masahiko Yakuwa; Tomohiko Kawanabe; Hisashi Igarashi; Hiroshi Ohno, all of Wako, Japan

[73] Assignee: Honda Giken Kogyo K.K., Tokyo, Japan

[21] Appl. No.: 341,635

[22] Filed: Apr. 21, 1989

[30] Foreign Application Priority Data

Apr. 25, 1988 [JP] Japan .............................. 63-101571
May 18, 1988 [JP] Japan .............................. 63-121386

[51] Int. Cl.⁵ .................... F02D 41/14; F02B 3/00; F02M 7/00
[52] U.S. Cl. ................................ 123/479; 123/440; 204/431
[58] Field of Search .............. 123/479, 440, 480, 489, 123/435; 340/635; 364/431.03, 431.11; 73/35; 204/195 S, 1 T, 426, 429, 406

[56] References Cited

U.S. PATENT DOCUMENTS

| | | | |
|---|---|---|---|
| 4,408,584 | 10/1983 | Yabuhara et al. | 123/440 |
| 4,521,769 | 6/1985 | Dudeck et al. | 340/635 |
| 4,724,814 | 2/1988 | Mieno et al. | 123/479 |
| 4,753,203 | 6/1988 | Yamada | 123/440 |
| 4,777,922 | 10/1988 | Mieno et al. | 123/479 |
| 4,780,826 | 10/1988 | Nakano et al. | 364/431.03 |
| 4,819,602 | 4/1989 | Mieno et al. | 123/479 |

Primary Examiner—Raymond A. Nelli
Attorney, Agent, or Firm—Arthur L. Lessler

[57] ABSTRACT

A method of detecting failure of an exhaust gas component concentration sensor for detecting concentration of a component of exhaust gases from an internal combustion engine. The method comprises the steps of: (1) applying a predetermined voltage to the sensor, (2) determining whether or not a change in an output voltage from the sensor caused by the application of the predetermined voltage to the sensor is smaller than a predetermined value, and (3) deciding that the sensor is faulty when the change in the output voltage is smaller than the predetermined value. A device for sensing concentration of a component of exhaust gases from an internal combustion engine comprising an electric resistance member connected in series between an electric current supply source and one of a pair of electrodes provided on a solid electrolytic element. A device for detecting failure of an exhaust gas component concentration sensing device comprising a constant voltage supply source for applying a predetermined voltage to the sensing device, and a switch connected between the constant voltage supply source and one of a pair of electrodes provided on an electrolytic element of the sensing device, for applying the predetermined voltage to the one of the electrodes when the switch is closed.

15 Claims, 12 Drawing Sheets

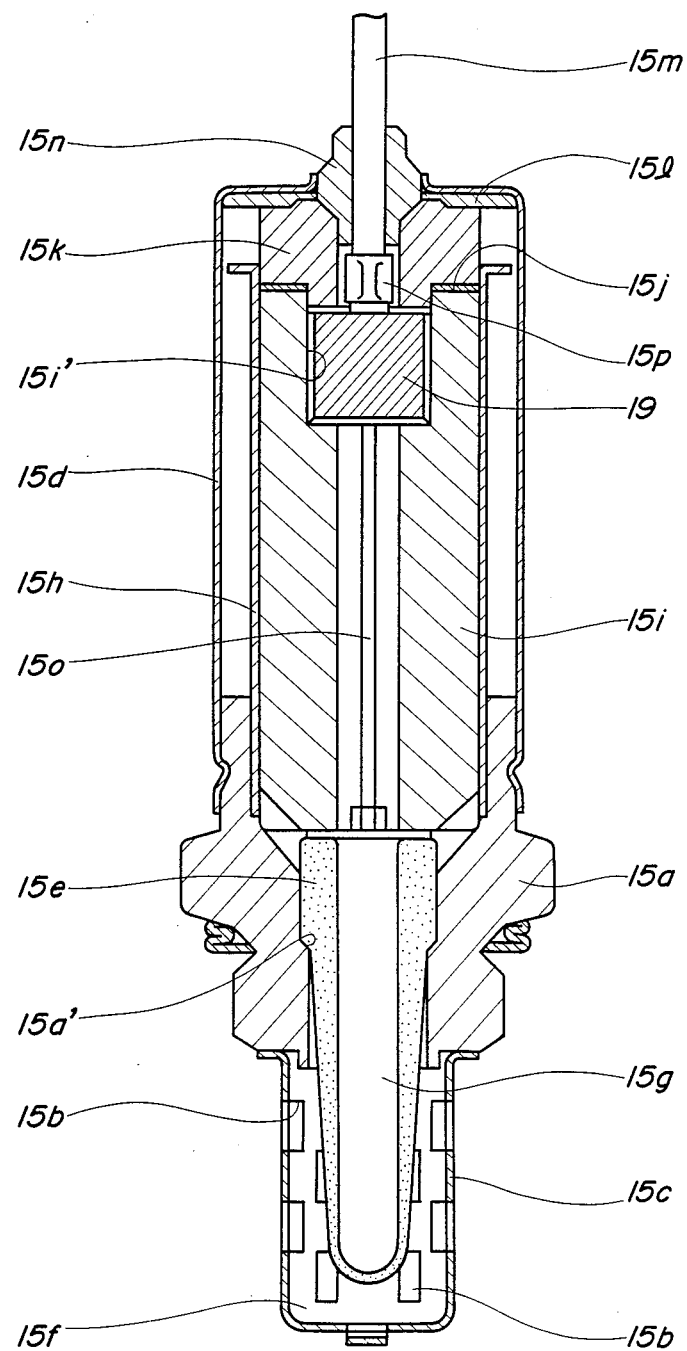

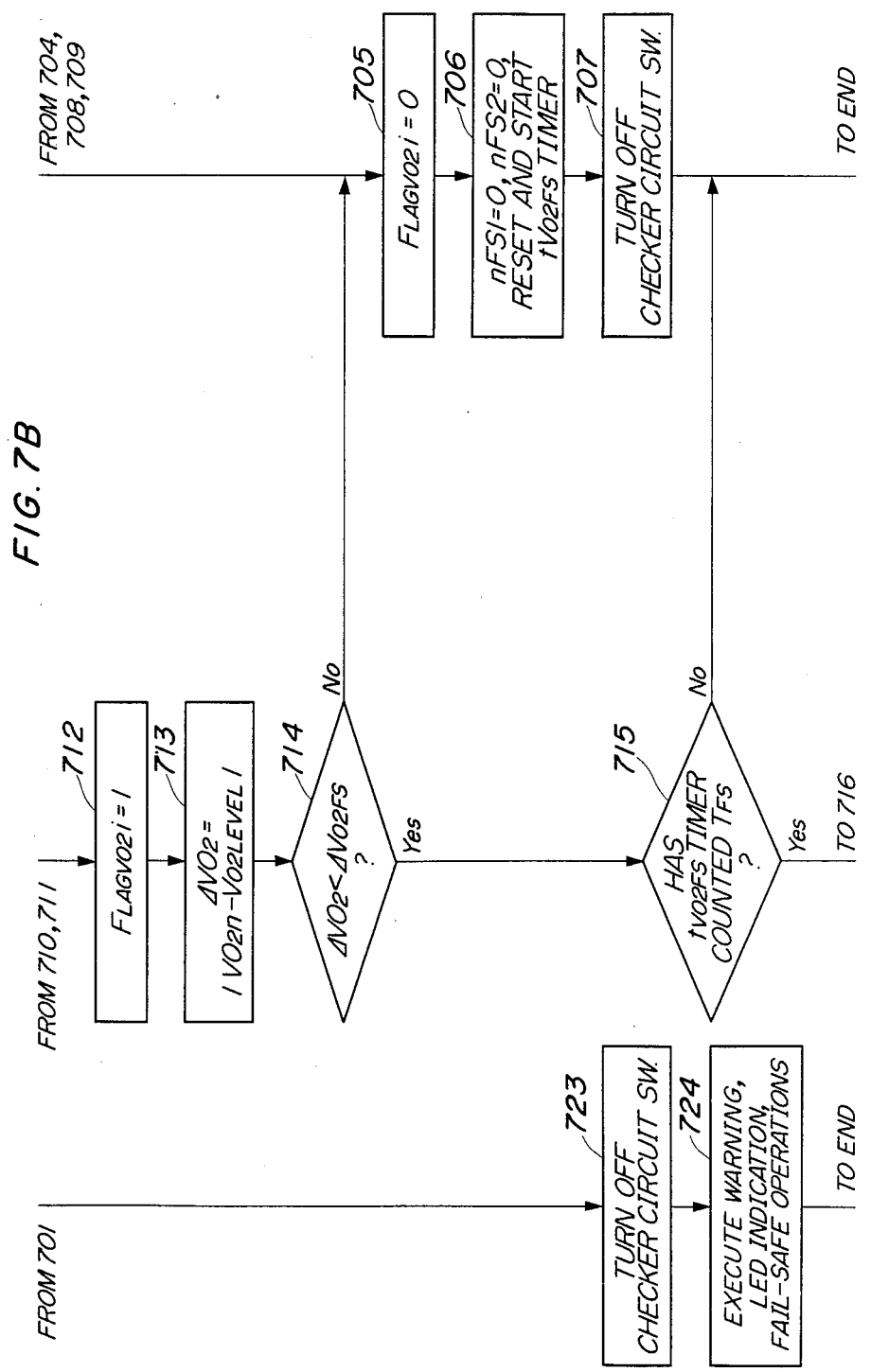

FIG. 7C

FROM 707, 715

| FIG.7A | FIG.7B | FIG.7C |

FIG. 7

FROM 715 → 716 TURN ON CHECKER CIRCUIT SW. → 717 tVO2FS=0 ? —Yes→ 718 nFS1=1 ? —No→ 719 nFS1=1 → 720 RESET AND START tFSW TIMER →

717 No → 
718 Yes → 721 tFSW=0 ? —Yes→ 722 nFS2=1 →
721 No →

FROM 724

FIG. 8
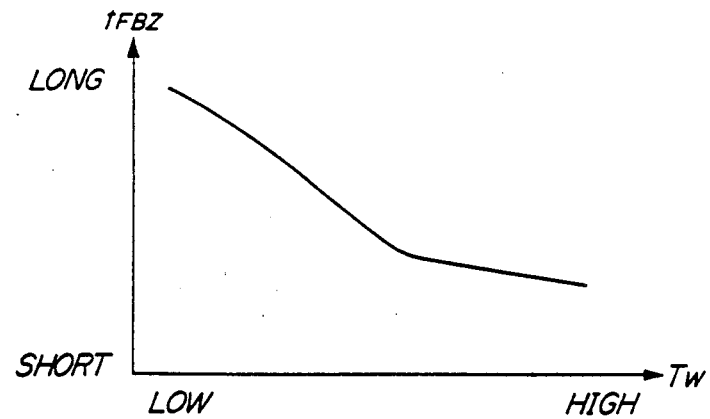
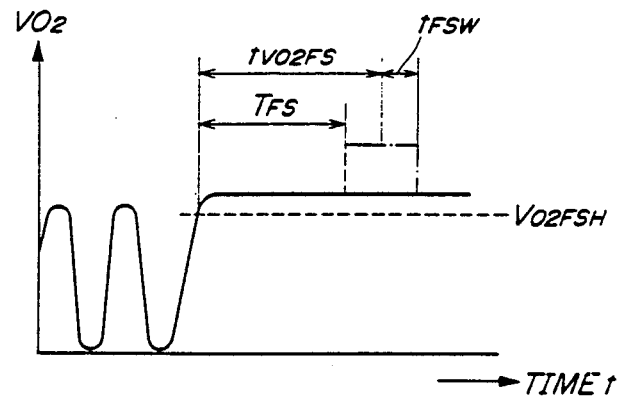
FIG. 9(a)
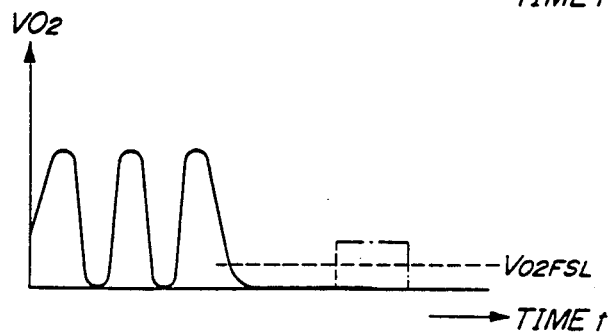
FIG. 9(b)

EXHAUST GAS COMPONENT CONCENTRATION SENSING DEVICE AND METHOD OF DETECTING FAILURE THEREOF

BACKGROUND OF THE INVENTION

This invention relates to an exhaust gas component concentration sensing device provided in a fuel supply control system for an internal combustion engine in which the air-fuel ratio of an air-fuel mixture supplied to the engine is controlled in response to the difference between the output voltage of the sensing device and a predetermined reference voltage, and a method of detecting failure of the sensing device, which detects disconnection or short-circuit in the sensing device from change in the output voltage thereof.

The exhaust gas component concentration sensing device has an improved construction which enables accurate and positive detection of failure thereof by the use of the failure detecting method of the invention.

In general, in order to control the air-fuel ratio of a mixture supplied to an internal combustion engine within a certain range having a desired value as its central value, concentration of a particular component contained in the exhaust gases, such as oxygen, is detected by a sensor, and responsive to the detected oxygen concentration, an air-fuel ratio correction coefficient is set to a proper value to thereby correct the air-fuel ratio of the mixture. The sensor for detecting the oxygen concentration in the exhaust gases, i.e. a so-called $O_2$ sensor is formed, for instance, of a solid electrolytic element of zirconia ($ZrO_2$), which has the characteristic that the electromotive force thereof changes sharply as the air-fuel ratio of the mixture changes across the stoichiometric ratio. The output voltage from the $O_2$ sensor is at a high level when the air-fuel ratio is richer than the stoichiometric ratio and at a low level when the air-fuel ratio is leaner than same. Failure of the $O_2$ sensor, such as disconnection and short-circuit, and deterioration thereof seriously affect the air-fuel ratio control. Therefore, it is necessary to always monitor an exhaust gas component concentration sensing device including the $O_2$ sensor so as to enable the air-fuel ratio control system to normally function based on a normal output signal from the sensing device.

To this end, a method of detecting failure of an exhaust gas component concentration sensor ($O_2$sensor) has been proposed e.g. by Japanese Patent Publication (Kokoku) No. 56-29100, in which a time interval at which inversion of the output voltage of the $O_2$ sensor takes place, i.e. the time interval between inversion of the output voltage from the high level to the low level and vice versa, is detected to thereby determine whether the $O_2$ sensor is faulty. Another method has been proposed, e.g. by Japanese Provisional Patent Publication (Kokai) No. 53-95431, in which the actual output voltage from the $O_2$ sensor is compared predetermined voltage higher than the upper limit of output voltage range (approximately 0.1 V to 1 V) that can be assumed during normal functioning of the $O_2$ sensor to thereby determine whether the $O_2$ sensor is faulty.

According to the former method, the time interval of inversion of an output voltage from a comparator to which the output from the $O_2$ sensor is applied is measured from an amount of charge accumulated in a capacitor. If the time interval is longer than a predetermined time interval, it is determined that the $O_2$ sensor is faulty. However, in this method, if a basic air-fuel ratio (e.g. corresponding to the basic value Ti of the fuel injection period $T_{OUT}$) is deviated from a proper value, the sensor output can stay on the lean side or rich side with respect to the stoichiometric air-fuel ratio over the predetermined time interval leading to an erroneous judgement that the $O_2$ sensor is faulty.

Specifically, if predetermined values of the basic value Ti of the fuel injection period stored in a map are deviated from proper values actually required by the engine, or if the opening area of a fuel injector or set fuel pressure from a fuel pressure regulator of the engine is deviated from a proper value due to manufacturing variations or aging even if the map values are proper, the air-fuel ratio may stay on the rich side or lena side even after a time period sufficient for inversion of the output voltage of the $O_2$ sensor has elapsed.

Thus, the proposed method of detecting the time interval of inversion of the output of the $O_2$ sensor for detecting failure of same may erroneously detect failure of the $O_2$ sensor in the above cases, even though the sensor is not faulty. In other words the proposed method is susceptible to deviation of the basic air-fuel ratio and variations etc. in component parts of the engine, which affects the accuracy and reliability of the failure detection.

On the other hand, according to the latter method in which it is determined that the $O_2$ sensor is faulty when the output voltage from the sensor is above a predetermined high voltage, e.g. 6 V, although it is able to detect disconnection in the $O_2$ sensor or its wiring, it is unable to detect short-circuit in the sensor or its wiring since the sensor output voltage drops to zero when the $O_2$ sensor or its wiring is short-circuited.

SUMMARY OF THE INVENTION

It is an object of the invention to provide a method of detecting failure of an exhaust gas component concentration sensing device for an internal combustion engine, which is capable of positively and promptly detecting disconnection and short-circuit in the sensing device as well as deterioration of the sensing device.

It is a further object of the invention to provide an exhaust gas component concentration sensing device which enables detection of not only disconnection but also short-circuit therein with improved accuracy.

According to a first aspect of the invention, there is provided a method of detecting failure of an exhaust gas component concentration sensor for detecting concentration to a component of exhaust gases from an internal combustion engine, the air-fuel ratio of an air-fuel mixture supplied to the engine being controlled in a feedback manner responsive to a difference between an output voltage from the sensor and a predetermined reference voltage value.

The method is characterized by comprising the steps of:

(1) applying a predetermined voltage to the sensor, (2) determining whether or not a change in the output voltage caused by the application of the predetermined voltage to the sensor is smaller than a predetermined value, and (3) deciding that the sensor is faulty when the change in the output voltage is smaller than the predetermined value.

Preferably, it is decided that the sensor is faulty when the change in the output voltage caused by the application of the predetermined voltage to the sensor has continued to be smaller than the predetermined value over a predetermined time period.

Further preferably, it is decided that the sensor is faulty when the change in the output voltage caused by the application of the predetermined voltage to the sensor has continued to be smaller than the predetermined value over a first predetermined time period, and further continued to be smaller than the predetermined value over a second predetermined time period following the first predetermined time period.

Preferably, the method comprises the steps of determining whether or not the output voltage is within a predetermined value range which can be assumed during normal operation of the engine, storing a value of the output voltage when the output voltage first falls outside the predetermined value range, determining whether a second difference between the stored value of the output voltage and each of subsequent actual values of the output voltage is smaller than a predetermined value, applying the predetermined voltage to the sensor when the second difference has continued to be smaller than the predetermined value over a first predetermined time period, and deciding that the sensor is faulty when the second difference has continued to be smaller than the predetermined value over a second predetermined time period after the application of the predetermined voltage to the sensor.

Further preferably, the steps (1) to (3) are carried out during the feedback control.

Further preferably, the steps (1) to (3) are carried out after a predetermined time period required for activation of the sensor has elapsed after the engine entered a predetermined feedback control region, when the feedback control is not being carried out.

According to a second aspect of the invention, there is provided a device for sensing concentration of a component of exhaust gases from an internal combustion engine, including:

an exhaust gas component concentration sensor having a solid electrolytic element, and a pair of electrodes provided on the solid electrolytic element, one of the electrodes being exposed to a reference gas, and the other of the electrodes being exposed to the exhaust gases; and electric current supply means for supplying a predetermined amount of electric current to the solid electrolytic element;

a voltage corresponding to the concentration of the exhaust gas component being developed between the electrodes when the predetermined amount of electric current is supplied to the solid electrolytic element from the electric current supply means.

The device is characterized by comprising an electric resistance member connected in series between the electric current supply means and one of the electrodes.

Preferably, the electric resistance member is connected in series between the electric current supply means and the one of the electrodes being exposed to the reference gas.

The above and other objects, features, and advantages of the invention will become more apparent from the ensuing detailed description taken in conjunction with the accompanying drawings.

BRIEF DESCRIPTION OF THE DRAWINGS

FIG. 4 is a longitudinal cross-sectional view of the sensor appearing in FIG. 3 and according to the invention;

Figure 3:
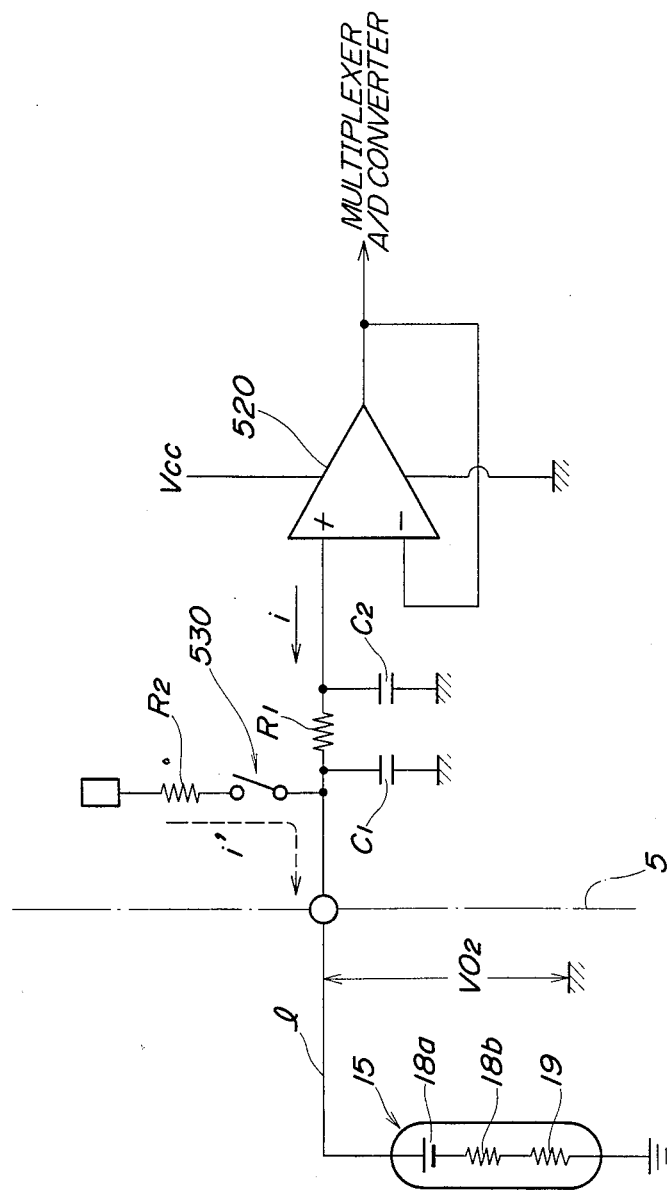
FIG. 3 is a circuit diagram showing the arrangement of an equivalent circuit of an $O_2$ sensor as the exhaust gas component concentration sensor according to the invention, a checker circuit, and a portion of the electronic control unit for receiving the output from the sensor.
Figure 5A:
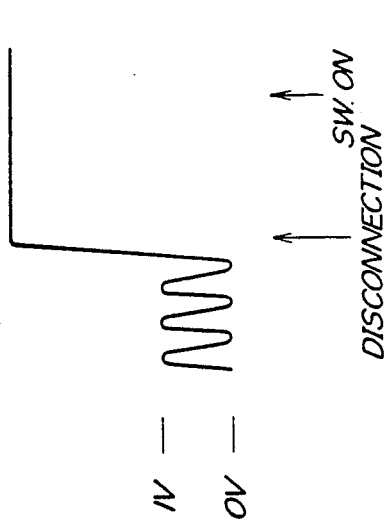
Figure 5B:
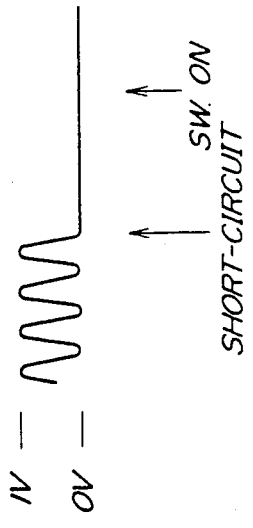
Figure 6A:
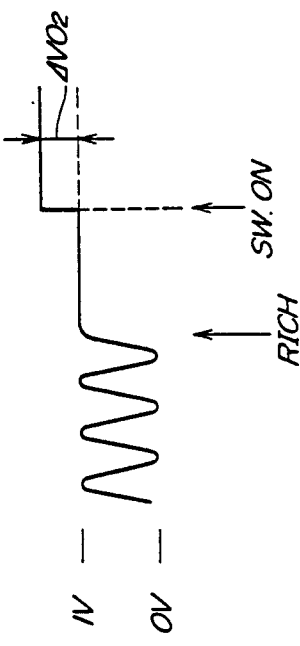
Figure 6B:
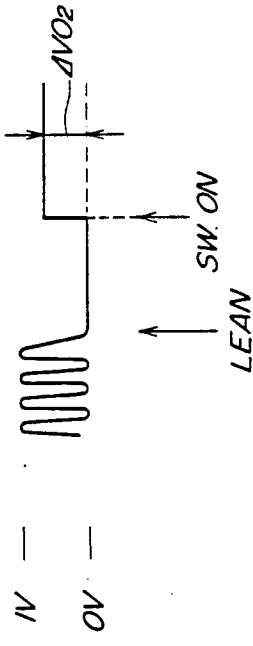
Figure 7A:
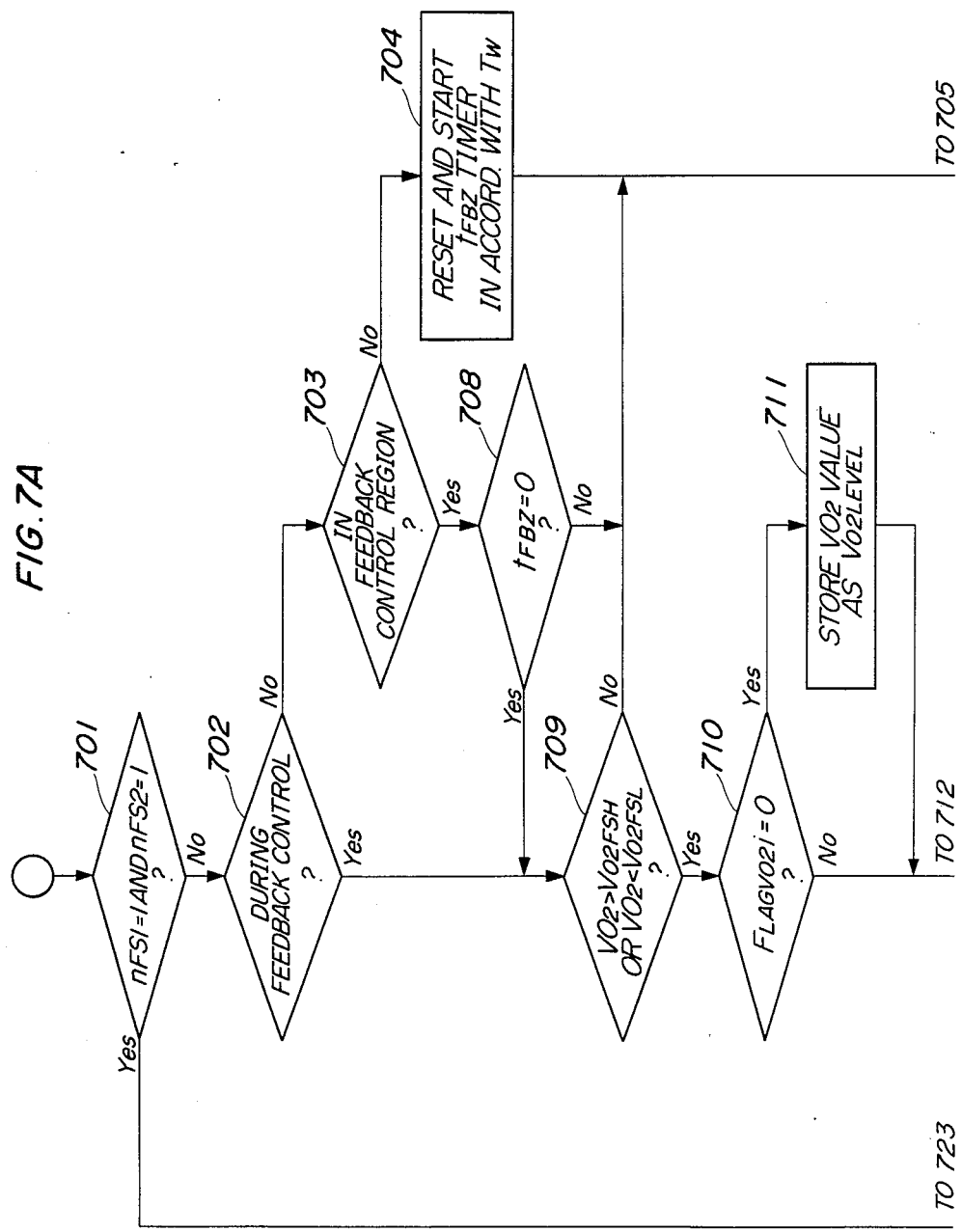
Figure 10:
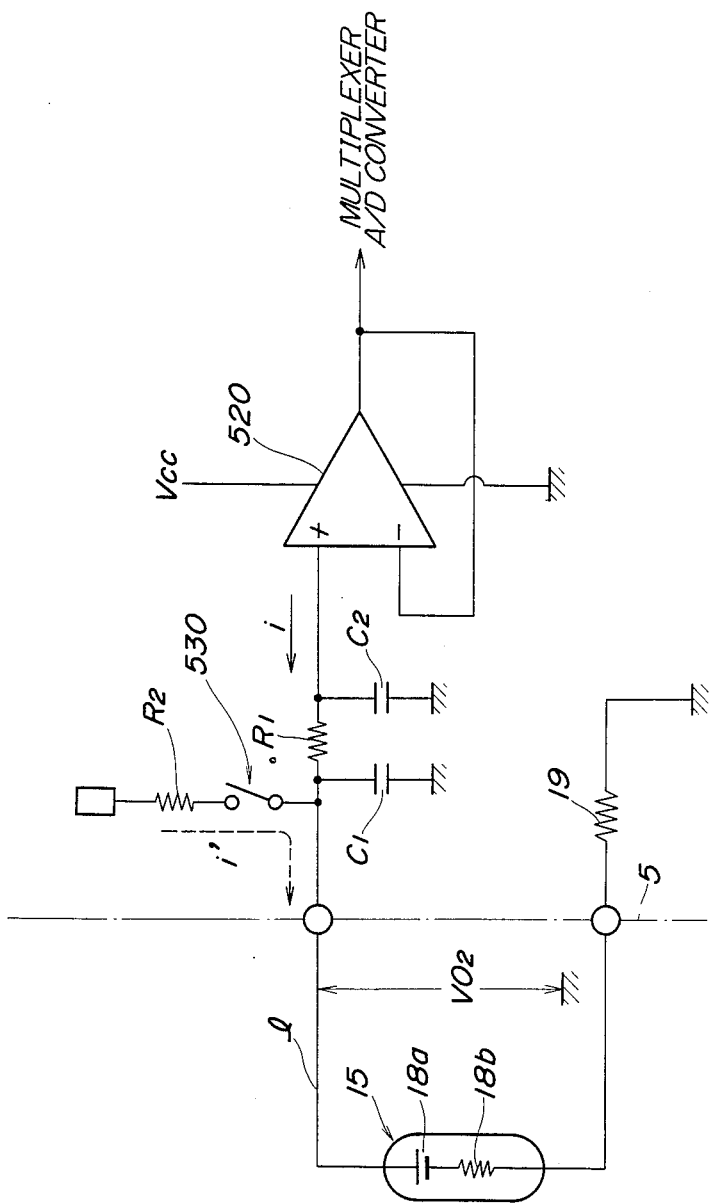
Figure 11:
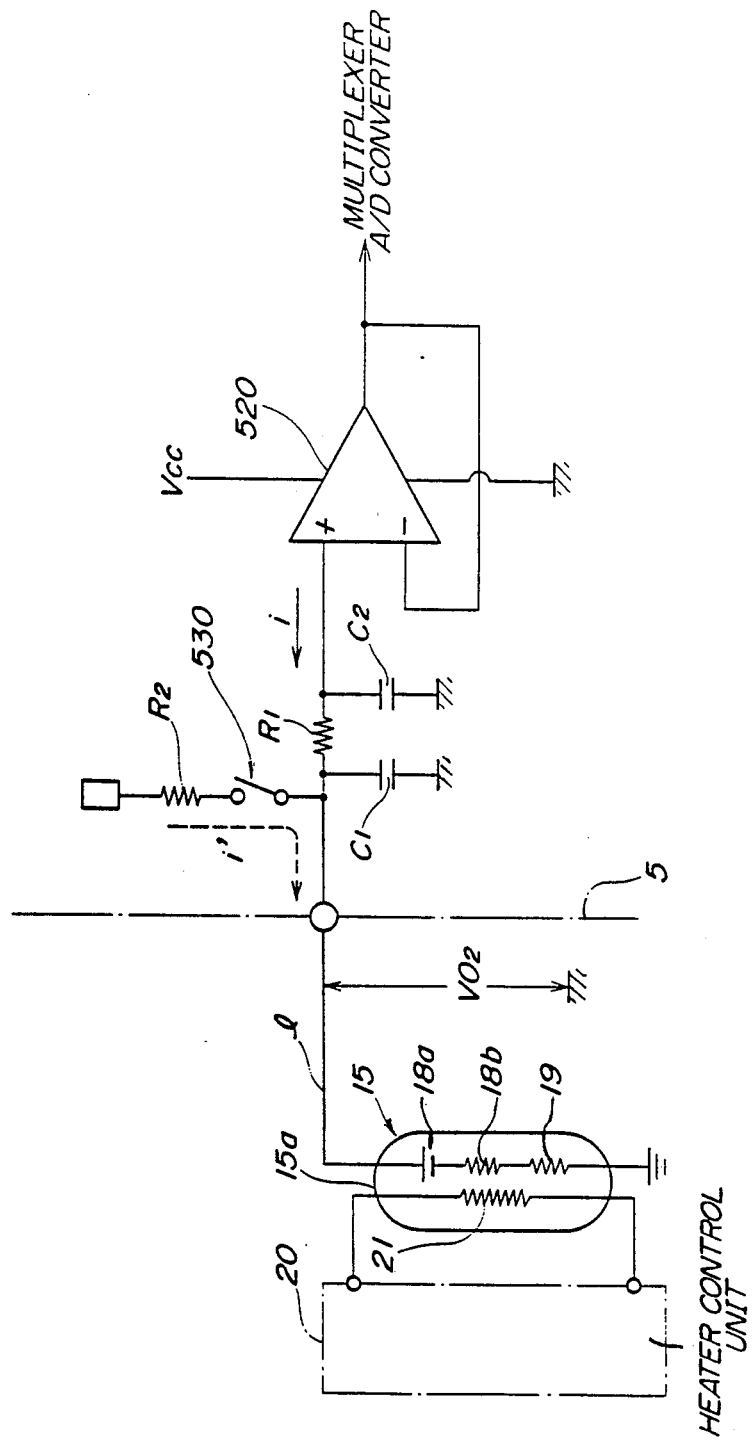
Figure 12:
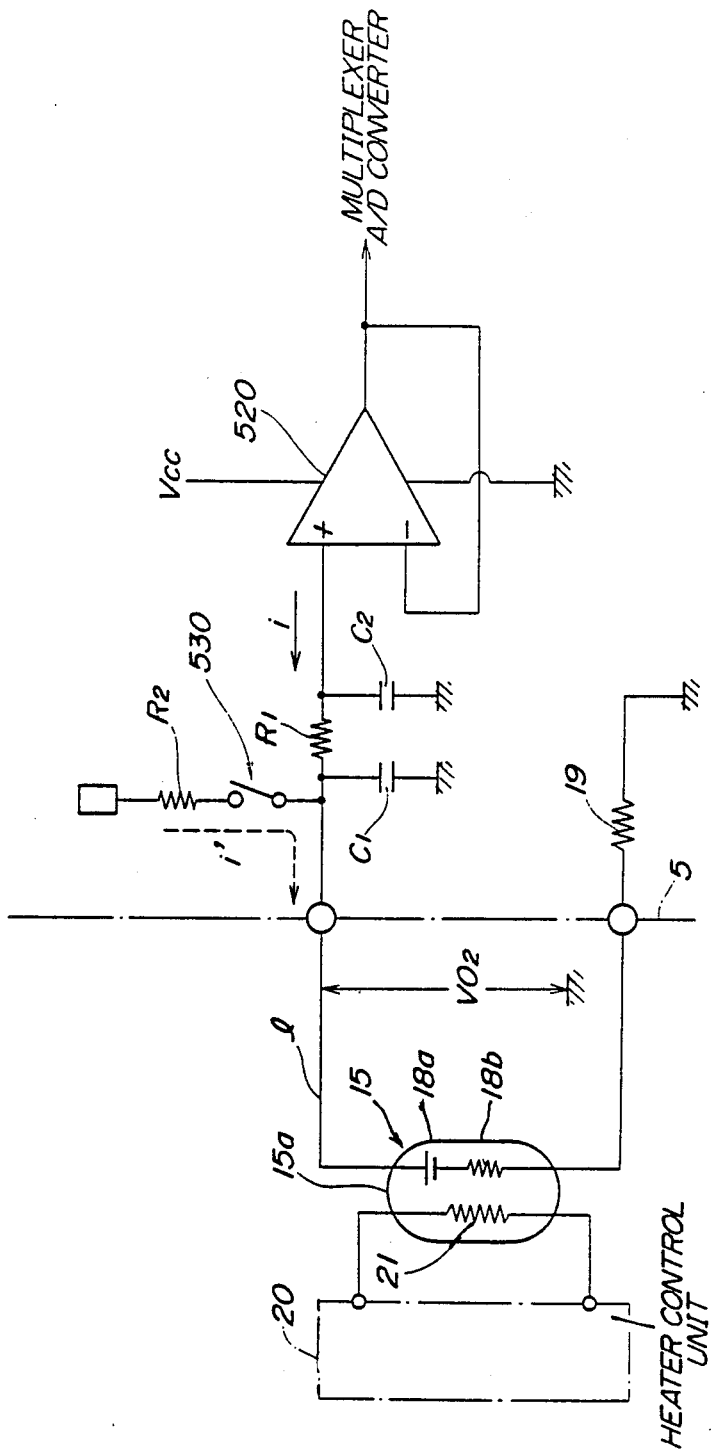

(a) and (b) of FIG. 5 are diagrams showing changes in the output characteristics of the sensor at the time of normal functioning thereof and at the time of disconnection thereof, respectively;

(a) and (b) of FIG. 6 are diagrams showing changes in the output characteristics of the sensor at the time of normal functioning thereof and at the time of short-circuit thereof, respectively;

FIGS. 7A through 7C are a flowchart showing a subroutine for detecting failure of the sensor according to the invention;

FIG. 8 is a diagram showing an example of a $T_W$-$t_{FBZ}$ table;

(a) and (b) of FIG. 9 are diagrams showing changes in the sensor output voltage $V_{O2}$ at the time of disconnection of the $O_2$ sensor and at the time of short-circuit thereof, respectively;

FIG. 10 is a similar view to FIG. 3, showing another embodiment of the $O_2$ sensor;

FIG. 11 is a similar view to FIG. 3, showing a further embodiment of the $O_2$ sensor; and FIG. 12 is a similar view to FIG. 3, showing a still further embodiment of the $O_2$ sensor.

DETAILED DESCRIPTION

The invention will now be described in detail with reference to drawings showing embodiments thereof.

Figure 1:
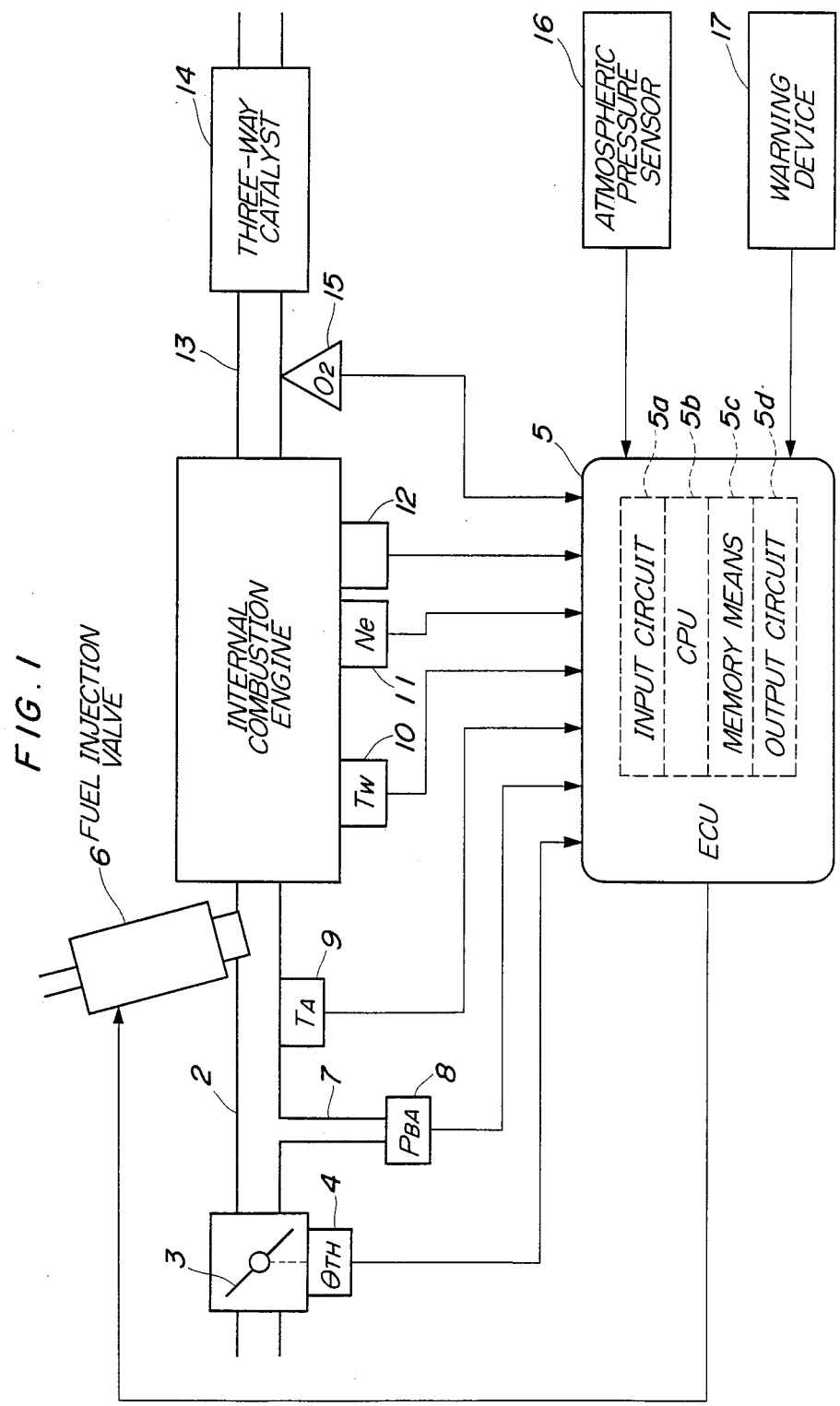
FIG. 1 is a block diagram illustrating the whole arrangement of a fuel supply control system for an internal combustion engine to which is applied the method of detecting failure of an exhaust gas component concentration sensor according to the invention.

Referring first to FIG. 1, there is illustrated the whole arrangement of a fuel supply control system for an internal combustion engine to which is applied the method of detecting failure of the exhaust gas component concentration sensor according to the invention. In the figure, reference numeral 1 designates an internal combustion engine which may be a four-cylinder type for instance, and to which is connected an intake pipe 2. A throttle valve 3 is arranged in the intake pipe 2. A throttle valve opening ($\theta_{TH}$) sensor 4 is connected to the throttle valve 3 for sensing its valve opening and is electrically connected to an electronic control unit (hereinafter called "the ECU") 5, to supply same with an electrical signal indicative of the throttle valve opening sensed thereby. The ECU 5 calculates desired values of the air-fuel ratio of a mixture to be supplied to the engine, and detects failure of the exhaust gas component concentration sensor, as hereinafter described.

Fuel injection valves 6 are arranged in the intake pipe 2 each at a location slightly upstream of an intake valve, not shown, of a corresponding one of the engine cylinders, not shown, and between the engine 1 and the throttle body 3, for supplying fuel to the corresponding engine cylinder. The fuel injection valves 6 are connected to a fuel pump, not shown, and are electrically connected to the ECU 5, in a manner having their valve opening periods or fuel injection quantities controlled by signals supplied from the ECU 5.

An absolute pressure ($P_{BA}$) sensor 8 communicates through a conduit 7 with the interior of the intake pipe 2 at a location downstream of the throttle valve 3, to sense absolute pressure in the intake pipe 2 and apply an electrical signal indicative of the detected absolute pressure to the ECU 5. Further, an intake air temperature ($T_A$) sensor 9 is arranged in the intake pipe 2 at a location downstream of the conduit 7 to sense intake air temperature ($T_A$) and apply an electrical signal indicative of the detected intake air temperature ($T_A$) to the ECU 5.

An engine coolant temperature ($T_W$) sensor 10, which may be formed of a thermistor or the like, is mounted on the cylinder block of the engine 1 in a manner embedded in the peripheral wall of an engine cylinder having its interior filled with coolant, of which an electrical output signal indicative of the sensed coolant temperature is supplied to the ECU 5.

An engine rotational speed (Ne) sensor 11 and a cylinder-discriminating (CYL) sensor 12 are arranged in facing relation to a camshaft, not shown, of the engine 1 or a crankshaft, not shown, of same. The Ne sensor 11 is adapted to generate one pulse at each of predetermined crank angles whenever the engine crankshaft rotates through 180 degrees, i.e. one pulse of the top-dead-center position (TDC) signal, which is supplied to the ECU 5. The CYL sensor is adapted to generate one signal pulse for discriminating a particular cylinder at a predetermined crank angle, which is also supplied to the ECU 5.

A three-way catalyst 14 is arranged in an exhaust pipe 13 extending from the cylinder block of the engine 1 for purifying components HC, CO and NOx contained in the exhaust gases.

An $O_2$ sensor 15 is inserted in the exhaust pipe 13 at a location upstream of the three-way catalyst 14 for detecting the concentration of oxygen contained in the exhaust gases and supplying an output voltage ($VO_2$) indicative of the detected concentration value to the ECU 5.

Further connected to the ECU 5 are other parameter sensors for determining operating conditions of the engine 1, including an atmospheric pressure sensor 16, for instance, which detects atmospheric pressure and applies a signal indicative of the detected atmospheric pressure to the ECU 5. Also connected to the ECU 5 is a fail-safe device, a warning device 17 for instance, which operates when a fault in the $O_2$ sensor or its wiring is detected. The warning device 17 carries out warning, such as raising of an alarming sound and indication of the fault by LED, based on a control signal supplied from the ECU 5.

The ECU 5 operates in response to various engine parameter signals inputted thereto from the above-mentioned various sensors to calculate the valve opening period $T_{OUT}$ of the fuel injection valves 6 by the use of the following equation:

$$T_{OUT} = Ti \times K_{O2} \times K_1 + K_2 \quad (1)$$

where Ti represents a basic value of the fuel injection period for the fuel injection valve 6, which is read from a memory device in the ECU 5 as a function of the engine speed Ne detected by the Ne sensor 11 and the absolute pressure $P_{BA}$ detected by the absolute pressure sensor 8. $K_{O2}$ represents an air-fuel ratio-correction coefficient, which is set depending on the oxygen gas concentration detected by the $O_2$ sensor 15 during feedback control of the air-fuel ratio, and is set, during open loop control of the air-fuel ratio, to an average value $K_{REF}$ of the air-fuel ratio correction coefficient $K_{O2}$ obtained during the feedback control. $K_1$ and $K_2$ represent other correction coefficients and correction variables which are calculated by the use of predetermined equations and/or maps based on engine parameter signals from the above-mentioned various sensors, i.e. the throttle valve opening ($\theta_{TH}$) sensor 4, absolute pressure ($P_{BA}$) sensor 8, intake air temperature ($T_A$) sensor 9, engine coolant temperature ($T_W$) sensor 10, engine speed (Ne) sensor 11, cylinder-discriminating (CYL) sensor 12, $O_2$ sensor 15, and atmospheric pressure sensor 16, so as to optimize operating characteristics of the engine, such as startability, exhaust emission characteristics, fuel consumption, and accelerability, in accordance with operating conditions thereof.

The ECU 5 supplies driving signals to the fuel injection valves 6 to open same over the valve opening period $T_{OUT}$ calculated as above.

Figure 2:
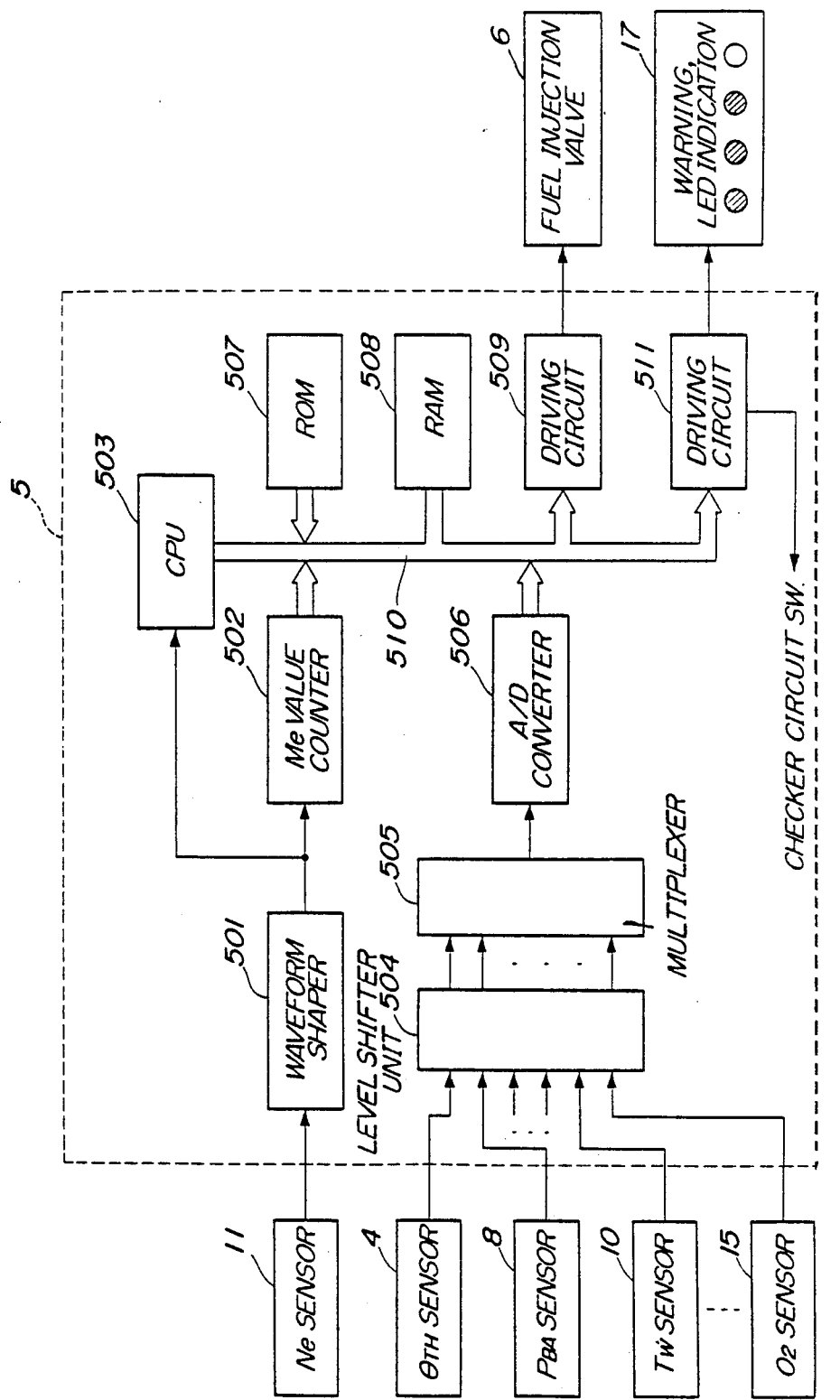
FIG. 2 is a block diagram illustrating the internal arrangement of an electronic control unit (ECU) appearing in FIG. 1.

FIG. 2 is a block diagram showing the internal arrangement of the ECU 5 appearing in FIG. 1. The TDC signal from the Ne sensor 11 in FIG. 1 is applied to a waveform shaper 501, wherein it has its pulse waveform shaped, and the shaped signal is supplied to a central processing unit (hereinafter called "the CPU") 503, as well as to an Me value counter 502. The Me value counter 502 counts the interval of time between a preceding pulse of the TDC signal and a present pulse of the same signal, inputted thereto from the Ne sensor 11. Therefore, its counted value Me corresponds to the reciprocal Of the actual engine speed Ne. The Me value counter 502 supplies the counted value Me to the CPU 503 via a data bus 510.

The respective output signals from the throttle valve opening ($\theta_{TH}$) sensor 4, the absolute pressure (PBA) sensor 8, the engine coolant temperature ($T_W$) sensor 10, the $O_2$ sensor 15, all appearing in FIG. 1, and other sensors are applied to a level shifter unit 504 to have their voltage levels shifted to a predetermined voltage level by the level shifter unit 504 and successively applied to an analog-to-digital converter (A/D converter) 506 through a multiplexer 505. The A/D converter 506 successively converts into digital signals analog output voltage from the aforementioned various sensors, and the resulting digital signals are supplied to the CPU 503 via the data bus 510.

Further connected to the CPU 503 via the data bus 510 are a read-only memory (hereinafter called "the ROM") 507, a random access memory (hereinafter called "the RAM") 508, and driving circuits 509 and 511. The ROM stores various programs to be executed in the CPU 503, such as a subroutine shown in FIG. 7 and described hereinafter, for detecting failure of the $O_2$ sensor and its wiring, various data, such as a map of basic values Ti of the fuel injection period and reference values $V_{O2FSH}$ and $V_{O2FSL}$ related to the output voltage of the $O_2$ sensor, described hereinafter, and various tables, such as a $T_W$- tFBZ table, while the RAM 508 temporarily stores results of calculations executed in the CPU 503, data read from the Me value counter 502 and the A/D converter, etc. The driving circuit 509 receives from the CPU 503 control signals indicative of the valve opening period $T_{OUT}$ calculated by the above equation (1), and supplies driving signals to the fuel injection valves to open same for the time period $T_{OUT}$.

The driving circuit 511 is for fail-safe purposes, and supplies a changeover control signal to a checker circuit switch (SW) employed for detecting failure of the O₂ sensor and its wiring to turn same on or off. The warning device 17 is connected to the driving circuit 511, and the ECU sends out a control signal for warning through the driving circuit 511 when failure of the O₂ sensor and its wiring has been detected.

FIG. 3 is a circuit diagram showing the arrangement of an equivalent circuit of the O₂ sensor as the exhaust gas component concentration sensor according to the invention, a checker circuit for detecting failure of the O₂ sensor, and a portion of the electronic control unit for receiving the output from the sensor. As shown in the figure, the O₂ sensor 15 has one end grounded to the wall of the exhaust pipe, and another end connected to the ECU 5 by way of a signal line 1. In order that disconnection or short-circuit between the O₂ sensor 15 and the ECU 5 may be detected more accurately and positively, an electric resistance member 19 having a predetermined resistance value is additionally incorporated in the O₂ sensor as an internal resistance for failure-detecting purposes, though the method of the invention described hereinafter can detect failure of the O₂ sensor and its wiring even without the electric resistance member 19.

More specifically, the O₂ sensor is essentially electrically composed of an electromotive force source 18a and an internal resistance 18b. However, in the O₂ sensor 15 according to the invention, the electric resistance member 19 is serially connected to the electromotive force source 18a and internal resistance 18b.

FIG. 4 shows an example of the construction of the O₂ sensor 15 with the electric resistance member 19 incorporated therein.

As shown in the figure, the O₂ sensor 15 has a housing 15a, which has an annular stepped shoulder 15a' for securing an oxygen concentration-detecting element (zirconia element) 15e therein, at a front or lower end portion thereof as viewed in FIG. 4, part of the front or lower end portion being inserted into the exhaust pipe 13. Mounted on a front or lower end of the housing 15a as viewed in FIG. 4 is a protection cover 15c, which has a plurality of through holes formed therein for passing exhaust gases therethrough. A cylindrical cap 15d is secured on the other or upper end of the housing 15a.

The zirconia element 15e, which is mainly composed of zirconium oxide in the form of a solid electrolyte and has a cylindrical shape with one closed end, is mounted inside the housing 15a and the protection cover 15c.

The zirconia element 15e has outer and inner surfaces thereof coated with platinum for serving as electrodes. A space 15f is defined within the cover 15c by the platinum-coated outer surface of the zirconia element 15e into which are introduced exhaust gases, while another space 15g is defined within the zirconia element 15e by the platinum-coated inner surface thereof into which is introduced air as a reference gas.

Mounted within the cylindrical cap 15d is an internal cylinder 15h which accommodates an oblong hollow cylindrical insulator 15i. A short hollow cylindrical insulator 15k is mounted on an upper end (as viewed in FIG. 4) of the oblong hollow cylindrical insulator 15i, via a washer 15j. A belleville spring 15l is interposed between an upper end surface of the short hollow cylindrical insulator 10k and an inner ceiling surface of the cylindrical cap 15d, for fitting the insulators 15i and 15k in place. Further, a grommet 15n, which is formed e.g. of fluororubber, is force fitted in a top end surface of the cylindrical cap 15d, for protecting a lead wire 15m by which the output of the O₂ sensor 15 is transmitted.

The lead wire 15m shown in FIG. 4 is the only lead wire that is connected to the O₂ sensor 15. The lead wire 15m is electrically connected to the electrode formed by the platinum-coated inner surface of the zirconia element 15e by way of an internal central electrode 15o and an internal central electrode 15p with a wave-shaped spring respectively arranged in the internal spaces within the insulators 5i, 15k. The electrode formed by the platinum-coated outer surface of the zirconia element 15e is grounded to the wall of the exhaust pipe 13 by way of the housing 15a. The electric resistance member 19 is arranged in a recess 15i' formed in the upper end face of the insulator 15i and electrically connected between the internal central electrodes 15o, 15p.

The electric resistance member 19 should be arranged at a location where it is less affected by heat from the exhaust gases. To this end, in the embodiment shown in FIG. 4, the member 19 is arranged at an end of the O₂ sensor 15 remote from the other end thereof where the zirconia element 15e and the protection cover 15c are arranged and exposed to heat from the exhaust gases.

The oxygen concentration in the exhaust gases is detected by the O₂ sensor constructed as above in the following manner: One of the two electrodes formed respectively by the inner and outer surfaces of the zirconia element 15e, i.e. the internal electrode formed by the inner surface in this embodiment, is exposed to air as the reference gas, while the other or external electrode is exposed to the exhaust gases. A predetermined amount of electric current is supplied from electric current supply means, referred to later, to the O₂ sensor. The oxygen concentration in the exhaust gases is detected from a voltage developed between the internal and external electrodes upon the supply of the electric current. More specifically, when the zirconia element 15e has its outer surface exposed to the exhaust gases from the exhaust pipe, and its inner surface exposed to air it acts as an oxygen cell to generate an electromotive force corresponding to the difference between oxygen concentration in the air and that in the exhaust gases in contact with the inner and outer surfaces of the zirconia element 15e, respectively. Thus a voltage depending on the oxygen concentration of the exhaust gases is developed between the internal and external electrodes. Further, the thus-generated voltage has the characteristic that it sharply changes as the air-fuel ratio of the mixture supplied to the engine changes across the stoichiometric ratio when the temperature of the zirconia element 15e is higher than a certain activation value. The oxygen concentration in the exhaust gases is detected by the ECU 5 utilizing the above characteristic. The ECU 5 is supplied with the output voltage from the O₂ sensor 15 through the lead wire 15m for carrying out the feedback control of the air-fuel ratio in response to the detected oxygen concentration. In the above-described so-called flow-in type O₂ sensor, according to the invention, the electric resistance member 19 is additionally provided so that failure of the O₂ sensor, such as disconnection or short-circuit thereof, can be more accurately detected.

Referring again to FIG. 3, a low-pass filter and an operational amplifier 520 are arranged within the ECU 5. The low-pass filter is composed of two capacitors $C_1$ and $C_2$, and a resistance $R_1$. The output voltage $V_{O2}$ from the O₂ sensor 15 is applied to a non-inverting input terminal of the operational amplifier 520 by way of the low-pass filter, amplified by the amplifier 520, and then supplied to the multiplexer 505 and A/D converter 506 in FIG. 2.

The operational amplifier 520 forms the electric current supply means which supplies electric current to the O₂ sensor 15 in the so-called "flow-in" manner.

Connected between the juncture of the capacitor $C_1$ with the resistance $R_1$ and an output terminal of a predetermined power source (e.g. battery in the vehicle) for supplying a predetermined constant voltage to the O₂ sensor, is a series circuit composed of a checker circuit switch 530 which is controllably closed and opened, and a resistance $R_2$. The checker circuit switch, which may be formed by any suitable conventional switching element, is controlled by a control signal from the driving circuit 511 in FIG. 2.

The checker circuit formed of the switch 530 etc. serves for detection of failure of the O₂ sensor 15, i.e. self-diagnosis, in such a manner that during a time interval when the output from O₂ sensor 15 remains at the same level, the switch 530 is closed to cause an increase in the electric current flowing into the O₂ sensor 15 and then the output voltage from the O₂ sensor is checked.

The principle of the failure detection according to the invention will now be described with reference to FIGS. 5 and 6.

When the self-diagnosis is not to be carried out, the checker circuit switch 530 is kept open. The output voltage $V_{O2}$ from the O₂ sensor 15 can be expressed by the electromotive force generated by the O₂ sensor and the electric current flowing from the operational amplifier 520 into the O₂ sensor 15, as follows:

$$V_{O2} = V_s + i \times r \quad (2)$$

where $V_s$ is the electromotive force (volt), i electric current from the operational amplifier 520, and r the sum of the internal resistance 18b of the O₂ sensor and the resistance value of the electric resistance member 19.

When the O₂ sensor 15 is in an activated state, the electric current i assumes a value of several tens of nA, and $i \times r$ assumes a value of several mV (which may be by setting the resistance value of the electric resistance member 19 to an appropriate value, e.g. from several k ohms to several tens of k ohms). Therefore, $V_{O2} \approx V_s$ holds, and accordingly the output voltage $V_{O2R}$ assumed when the air-fuel ratio is richer than the stoichiometric value is nearly equal to 1 volt, whereas the output voltage $V_{O2L}$ assumed when the former is leaner than the latter is nearly equal to 0 volt. That is, when the O₂ sensor is normally functioning, the output voltage $V_{O2}$ is repeatedly inverted, as shown in FIGS. 5 and 6, according to the output characteristic of the so-called flow-in type O₂ sensor as in the embodiment of FIG. 3.

When the switch 530 is closed, the predetermined voltage from the predetermined power source is additionally applied to the O₂ sensor 15 through the closed switch. On this occasion, electric current i' flows through the resistance $R_2$ so that the total current flowing into the O₂ sensor 15 is equal to the sum of i+i'. Therefore, the output voltage $V_{O2}$ from the O₂ sensor can be expressed as follows:

$$V_{O2} = V_s + (i+i') \times r \quad (3)$$

Assuming that the electric current i' flowing through the closed switch 530 assumes several tens of μA, i×r will assume a value of several mV when the O₂ sensor 15 is in an activated state, as stated before. Therefore, the output voltage $V_{O2}$ can also be expressed as follow:

$$V_{O2} \approx V_s + i' \times r \quad (4)$$

It will be understood from the above that when there is no fault in the signal line 1, that is, there is neither disconnection nor short-circuit in the signal line, if the switch 530 is turned on, the output voltage $V_{O2}$ increases by an amount of $\Delta V_{O2} = i' \times r$, as shown in (a) of FIG. 5 and (a) of FIG. 6. The amount $\Delta V_{O2}$ is of the order of 0.1–1.0 volt.

Thus, when there is no fault in the O₂ sensor 15 and its wiring, the normality can be ascertained by monitoring a change in the voltage $V_{O2}$ caused by the turning-on of the switch 530.

On the other hand, when there is a fault in the O₂ sensor 15, even if the switch 530 is turned on, there occurs no change in the output voltage $V_{O2}$. Thus, it is possible to detect a fault in the O₂ sensor 15 by checking whether or not the output voltage $V_{O2}$ has changed after turning-on of the switch 530.

More specifically, in the event of a disconnection in the signal line, the resistance value of the O₂ sensor will increase to infinity with respect to the ECU 5 side. Accordingly, irrespective of the magnitude of current flowing into the sensor, that is, irrespective of whether the switch 530 is closed or open, the voltage at the input side of the ECU 5 is expressed as follows:

$$V_{O2(ECU)} = \infty \times i \approx \infty \times (i+i') = \infty \quad (5)$$

In the actual circuit configuration of FIG. 3, the voltage $V_{O2(ECU)}$ will be equal to a positive output voltage supplied from the power source to the operational amplifier 520, i.e. the maximum output voltage from the amplifier 520 [(b) of FIG. 5].

Thus, in the event of a disconnection in the 02 sensor 15 or its wiring, the voltage $V_{O2(ECU)}$ increases up to the positive output voltage from the power source or the maximum output voltage to be held thereat, and then it will not change even if the switch 530 is closed. From this increased constant voltage $V_{O2(ECU)}$ which is different from the voltage level assumed during normal functioning of the O₂ sensor as shown in (a) of FIG. 5, it is possible to positively determine the occurrence of the disconnection.

Further, the arrangement of the invention can also detect the occurrence of a short-circuit in the O₂ sensor or its wiring by closing the switch 530, as follows:

In the event that the signal line 1 is shorted to the ground, the voltage level at the input side of the ECU 5 drops down to the ground potential to be held thereat, as shown in (b) of FIG. 6, so that irrespective of the magnitude of current flowing into the O₂ sensor 15, that is, irrespective of whether the switch 530 is closed or open, $V_{O2} \approx 0$ holds, and no change occurs in the voltage level of the input side of the ECU 5. Thus, it is possible to positively determine the occurrence of a short-circuit in the O₂ sensor or its wiring from the thus decreased constant voltage level at the input side of the ECU 5 which is different from the voltage level assumed during normal functioning of the O₂ sensor as shown in (a) of FIG. 6.

As described above, by virtue of the arrangement of the checker circuit of FIG. 3, insofar as there is no fault in the $O_2$ sensor 15 and its wiring, when the switch 530 is closed to cause increased current to flow into the $O_2$ sensor 15, there occurs a change in the voltage level $V_{O2(ECU)}$ at the input side of the ECU 5 by the amount $\Delta V_{O2}$ as shown in (a) of FIG. 5 and (a) of FIG. 6, whereas if there is an abnormality, such as a disconnection and a short-circuit in the $O_2$ sensor and its wiring, even if the switch 530 is closed, no change corresponding to the amount $\Delta V_{O2}$ takes place in the voltage level $V_{O2(ECU)}$ as shown in (b) of FIG. 5 and (b) of FIG. 6. Therefore, by closing the switch 530 within a certain time interval during which the $O_2$ sensor 15 is not inverted and then monitoring the change in the voltage level $V_{O2(ECU)}$ at the input side of the ECU 5, it is possible to accurately determine a fault, and moreover the kind of such fault.

FIG. 7 shows a program for detecting failure of the $O_2$ sensor 15 based on the above-described principle according to the method of the present invention. This program is executed whenever a pulse of the TDC signal is supplied to the ECU 5.

In the figure at a step 701, it is determined whether or not both first and second flags $\eta FS1$ and $\eta FS2$ for failure determination have been set to 1. If the answer to the question to the step 701 is No, the program proceeds to a step 702.

At the step 702, it is determined whether or not the air-fuel ratio feedback control based upon the $0_2$ sensor output is being executed. If the answer to the question of the step 702 is Yes, the program proceeds to steps 709 et seq. referred to hereinafter, while if the answer is No, it is further determined at a step 703 whether or not the engine is in an air-fuel ratio feedback control region.

If the answer to the question of the step 703 is No, a tFBZ timer which has a timer value tFBZ thereof set in accordance with the engine coolant temperature $T_W$ is reset and started at a step 704. FIG. 8 shows a $T_W$-tFBZ table used in the step 704 in which the timer value tFBZ is set to shorter values as the $T_W$ value is greater, i.e. as the engine coolant temperature is higher.

If the air-fuel ratio feedback control is not being executed and the engine is not in the air-fuel ratio feedback region, at a step 705 following the step 704, a flag $F_{LAGVO2i}$ used for determination at a step 710 referred to hereinafter, is set to 0, and then at a step 706, both the first and second flags $\eta FS1$ and $\eta FS2$ for failure determination are set to 0. and a tVO2FB timer (down counter) whose timer value is interrogated at steps 715 and 717, referred to hereinafter, is set to a predetermined time period (e g. 4.5 seconds) and started. Further, at a step 707, the switch 530 of the checker circuit shown in FIG. 3 is held in the OFF state, followed by terminating the present program.

If the answer to the question of the step 703 is Yes, i.e. if the engine is in the air-fuel ratio feedback control region even if the feedback control is not being executed, it is determined at a step 708 whether or not the predetermined period of time set by the $t_{FBZ}$ timer in accordance with the engine coolant temperature $T_W$ at the step 704 has elapsed. If the answer to the question of the step 708 is No, i.e. if the predetermined time period has not elapsed, the aforementioned steps 705 to 707 are executed, followed by terminating the program. If the predetermined time period has elapsed, the program proceeds to the steps 709 et seq.

The reason for the provision of the steps 703, 704 and 708 in addition to the step 702, in which is determined whether or not the $O_2$ feedback control is being executed, is as follows:

The determination at the step 702 is executed based upon various conditions, such as whether the engine coolant temperature is higher than a predetermined value, and whether the $O_2$ sensor has become activated. If it is determined that the feedback control is being carried out in reality, self-diagnosis of the $O_2$ sensor and its wiring is carried out at the steps 709 et seq. However, even if the feedback control is not being carried out, if it is determined that the engine is in the air-fuel ratio feedback control region defined by the intake pipe absolute pressure $P_{BA}$ and the engine rotational speed Ne, the self-diagnosis of the $O_2$ sensor 15 and its wiring may be carried out when the answer to the question of the step 708 is affirmative or Yes, which enables to regard the $O_2$ sensor 15 as activated.

Specifically, a time period required for activation of the $O_2$ sensor 15 is almost determined by the engine temperature. Therefore, the predetermined time period is set by the tFBZ timer depending on the engine coolant temperature $T_W$ in such a manner that it is equal to the time period required for activation of the $O_2$ sensor, i.e. the higher the engine coolant temperature $T_W$, the shorter the timer-set predetermined time period $t_{FBZ}$. If the time period $t_{FBZ}$ has elapsed after it was determined that the engine is in the air-fuel ratio feedback control region, the steps 709 et seq. for self-diagnosis of the $O_2$ sensor 15 and its wiring are carried out by regarding the $O_2$ sensor as activated.

Therefore, the resetting and starting of the $t_{FBZ}$ timer in response to the $T_W$ value is executed even during starting of the engine.

Thus, the inconvenience that the failure detection of the $O_2$ sensor can be carried out only when the feedback control is being carried out can be eliminated by virtue of the steps 703, 704, and 708, making it possible to carry out self-diagnosis of the $O_2$ sensor and its wiring sooner.

At the step 709, it is determined whether or not the output voltage $V_{O2}$ of the $O_2$ sensor is higher than a predetermined upper limit value $V_{O2FSH}$ (e.g. 0.9 V) or the output voltage $V_{O2}$ is lower than a predetermined lower limit value $V_{O2FSL}$ (e g. 0.1 V) (see (a) and (b) of FIG. 9). If the answer to the question of the step 709 is No, i.e. if $V_{O2FSL} \leq V_{O2} \leq V_{O2FSH}$, it is judged that the output voltage $V_{O2}$ is in a value range which can be assumed during normal operation of the engine 1, and hence that the $O_2$ sensor 15 is in normal operation, and the steps 705 et seq. are executed without starting the self-diagnosis the $O_2$ sensor and its wiring, followed by terminating the present program.

On the other hand, if the answer to the question of the step 709 is Yes, i.e. if $V_{O2} > V_{O2FSH}$ ((a) of o FIG. 9) or $V_{O2} < V_{O2FSL}$ ((b) of same), this indicates the possibility of disconnection or short-circuit in the $O_2$ sensor and its wiring, and therefore steps 710 et seq. are carried out.

First, at a step 710, it is determined whether or not the flag $F_{LAGVO2i}$ has been set to 0. If the answer to the question of the step 710 is Yes, i.e. if the present loop is the first loop after the output voltage $V_{O2}$ has fallen outside the value range defined by the predetermined higher and lower limit values $V_{O2FSH}$ and $V_{O2FSL}$, the $V_{O2}$ value is stored as $V_{O2LEVEL}$ at a step 711, and then the flag $F_{LAGVO2i}$ is set to 1 at a step 712. In other words, if the output voltage $V_{O2}$ has started to assume a value outside the normal value range, the $V_{O2}$ value is stored and the flag $F_{LAGVO2i}$ is set to 1. In the following loops, since the flag $F_{LAGVO2i}$ has been already set to 1, the answer to the question of the step 710 should be No, and therefore the program jumps over the step 711 to the step 712. The $V_{O2}$ value stored at the step 711 is used as a reference value for monitoring change in the output voltage $V_{O2}$ to thereby determine failure of the $O_2$ sensor and its wiring.

At a step 713 following the step 712, the absolute value $\Delta V_{O2}$ of the difference between the $V_{O2}$ value detected in the present loop and the $V_{O2LEVEL}$ stored at the step 711 as the reference value is calculated, and then at a step 714, it is determined whether or not the $\Delta V_{O2}$ value is smaller than a predetermined variation $\Delta V_{O2FS}$. As described hereinbefore with reference to FIGS. 5 and 6. the predetermined variation $\Delta V_{O2FS}$ is set to an appropriate value depending on possible variation in the output voltage $V_{O2}$ which may occur when the checker circuit switch 530 is closed during normal operation of the $O_2$ sensor (specifically, depending on the output voltage of the power source, the resistance $R_2$, the kind of the $O_2$ sensor used, etc.). The appropriate value should be a value smaller than the possible variation in the output voltage $V_{O2}$.

If the present loop is a loop in which the $V_{O2}$ value is stored as $V_{O2LEVEL}$ at the step 711, the answer to the question of the step 714 should be Yes, and therefore the program proceeds to a step 715 where it is determined whether or not a predetermined time period $T_{FS}$ (e.g. 4.0 seconds) shorter than the predetermined time period $t_{VO2FS}$ set by the $t_{VO2FS}$ timer has elapsed (see (a) of FIG. 9).

If the answer to the question of the step 715 is No, i.e if the predetermined time period $T_{FS}$ has not elapsed, the program is terminated immediately. In any subsequent loop, if the state of $\Delta V_{O2} < V_{O2FS}$ is continued, i.e. if the output voltage $V_{O2}$ is not changed at all or changed by a value smaller than $\Delta V_{O2FS}$, and at the same time if the predetermined time period $T_{FS}$ has elapsed and the answer to the question of the step 715 has become Yes, the switch 530 of the checker circuit is turned on or closed (step 716).

Then, after the switch of the checker circuit has thus been turned on, it is determined at a step 717 whether or not the rest of the predetermined time period $t_{VO2FS}$, i.e. $t_{VO2FS}$-$T_{FS}$ (0.5 seconds) has elapsed. If the answer to the question of the step 717 is No, i.e. if the predetermined time period $t_{VO2FS}$ has not elapsed after the $t_{VO2FS}$ timer was started, the program is terminated immediately.

When the switch 530 of the checker circuit is turned on as described, if the $O_2$ sensor and its wiring are normally functioning without suffering from disconnection or short-circuit, the output voltage $V_{O2}$ should change in a predetermined manner as illustrated in (a) of FIG. 5 or (a) of FIG. 6. That is, in the following loop, the $V_{O2}$ value will undergo a change indicated by the broken lines in (a) or (b) of FIG. 9. Accordingly, it is determined at the step 714 that the variation $\Delta V_{O2}$ of the output voltage $V_{O2}$ exceeds the predetermined value $\Delta V_{O2FS}$, with the result that the result of determination at the step 714 during normal operation of the $O_2$ sensor and its wiring becomes No, followed by executing the steps 705 to 707 and terminating the program. Specifically, the flags $F_{LAGVO2i}$, $\eta FS1$, and $\eta FS2$, $t_{VO2FS}$ timer, and the checker circuit switch 530 are all reset, terminating the self-diagnosis of the $O_2$ sensor and its wiring in the case of normal functioning thereof.

On the other hand, if the answer at the step 714 is Yes in spite of the fact that the checker circuit switch 530 has been turned on, and at the same time if this continues for a predetermined time period ($t_{VO2FS}$- $T_{FS}$) or longer, i.e. if the answer to the question at the step 717 becomes Yes, it is judged that the $O_2$ sensor or its wiring is faulty, and then steps 718 et seq. are executed to finally determine that there is failure in the $O_2$ sensor or its wiring.

According to the present embodiment of the invention, determination of failure of the $O_2$ sensor and its wiring is carried out twice. Specifically, at a step 718, it is determined whether or not the first flag $\eta FS1$ for failure determination has been set to 1. If the answer to the question of the step 718 is No, the program proceeds to a step 719, where the first flag $\eta FS1$ is set to 1, and at the following step 720, a $T_{FSW}$ timer for counting a predetermined time period $T_{FSW}$ (e.g. 0.5 seconds) is reset and started, followed by terminating the program.

In the following loop the answer to the question of the step 718 should become Yes, and then the program proceeds to a step 721, where it is determined whether or not the predetermined time period $T_{FSW}$ has elapsed. If the answer to the question of the step 721 is No, i.e. if the predetermined time period $T_{FSW}$ has not elapsed, the program is immediately terminated, while if the answer is Yes, i.e. if the predetermined time period $T_{FSW}$ has elapsed, the second flag $\eta FS2$ is set to 1 at a step 722, followed by terminating the program.

After the second flag $\eta FS2$ has thus been set to 1 at the step 722, the result of determination at the step 701 in the following loop should become Yes, whereby it is finally determined that the $O_2$ sensor or its wiring is suffering from disconnection or short-circuit. Then at a step 723, the checker circuit switch 530 is turned off, and at a step 724, the occurrence of failure of the $O_2$ sensor or is wiring is notified by a warning sound and indication by LED, and other necessary fail-safe actions are carried out, followed by terminating the program.

Thus, the self-diagnosis of the $O_2$ sensor and its wiring in the case of failure thereof is completed.

According to the above-described method of the invention, failure of the $O_2$ sensor and its wiring is detected by applying a predetermined voltage to the sensor by the checker circuit switch 530, and then detecting the variation $\Delta V_{O2}$ of the $V_{O2}$. Therefore, it is possible to detect failure in both the cases of disconnection and short-circuit by the same detecting procedure. Further, any influence of a deviation in the basic air-fuel ratio on the failure detection can be excluded to thereby enable to carry out positive failure detection of the $O_2$ sensor and its wiring.

In particular, when the engine undergoes hot restart after high-speed running of the vehicle, the air-fuel mixture supplied to the engine becomes rich due to fuel attached to the intake pipe. When the vehicle is running in high altitudes, the inversion of output of the $O_2$ sensor 15 is not carried out as usual. Even in such cases, according to the invention, the failure of the $O_2$ sensor 15 can be positively detected while discriminating an actual failure from an apparent and false failure resulting from the cases.

Further, according to the invention, not only the disconnection and short-circuit of the $O_2$ sensor 15 but also deterioration of same can be detected.

Specifically, as the O$_2$ sensor 15 is deteriorated, the value of internal resistance (18b in the case of a conventional O$_2$ sensor, and 18b+19 in the case of the O$_2$ sensor according to the invention) increases, so that even if the checker circuit switch is turned on to increase the amount of electric current supplied thereto, the resulting variation of the V$_{O2}$ becomes almost inappreciably small.

Therefore, by setting the predetermined variation $\Delta V_{O2FS}$ used at the step 714 at a suitable value taking the above characteristic of the O$_2$ sensor into consideration, deterioration of the O$_2$ sensor can also be detected.

Further, in the above-described embodiment, the failure detection or determination is carried out twice by means of the two flags $\eta FS1$ and $\eta FS2$. Therefore, even if one of the flags is erroneously set to 1 due to noise etc., an erroneous diagnosis can be prevented. In the meanwhile, although the failure detection or determination is carried out twice, it takes a short time period (5 seconds in the embodiment) to detect failure of the O$_2$ sensor and its wiring including deterioration of the O$_2$ sensor. Therefore, the method of the invention also meets the requirement of prompt detection of failure.

Further, the method of the invention may be applied to the conventional O$_2$ sensor. However, if the O$_2$ sensor is constructed as shown in FIGS. 3 and 4, more positive failure detection can be carried out. Specifically, according to the O$_2$ sensor 15 of the invention, the electric resistance member 19 is connected in series between the electric current supply means and one of the electrodes of the zirconia element 15e. Therefore, when the O$_2$ sensor 15 and its wiring is normally functioning, change in the output voltage V$_{O2}$ at the time electric current is additionally supplied by turning-on of the checker circuit switch 530 can be accurately detected to thereby ensure positive detection of the failure of the O$_2$ sensor and its wiring. Particularly, when the O$_2$ sensor becomes very hot, the internal resistance of the O$_2$ sensor 15 generally tends to decrease to a very small value. Therefore, even if the flow-in current i' is supplied thereto as described with reference to FIG. 3, the variation $\Delta V_{O2}$ in the output voltage may not show a normal appreciable value because the internal resistance of the O$_2$ sensor is very small. In such a case, it, may be erroneously judged that there is a short circuit in the O$_2$ sensor or its wiring in spite of the fact that the O$_2$ sensor and its wiring are normal. If electric current much greater than the flow-in current i' is caused to flow in the O$_2$ sensor 15, an appreciable value of $\Delta V_{O2}$ may be produced even when the O$_2$ sensor is hot. However, if too great electric current is supplied, the O$_2$ sensor will be deteriorated and become incapable of performing its function.

In contrast, in the case of the O$_2$ sensor according to the invention described with reference to FIGS. 3 and 4, the electric resistance member 19 is added in series to the internal resistance 18b. Therefore, even if the internal resistance 18b of the O$_2$ sensor 15 decreases at high temperature, the decrease in the internal resistance 18b may be covered by the electric resistance member 19. Under any engine load condition, by supplying a predetermined amount of current i' to the O$_2$ sensor, it is possible, by virtue of the electric resistance member 19, to always obtain a value of $\Delta V_{O2}$ which is greater than a certain value required for determining that the O$_2$ sensor and its wiring are normal.

Further, if the electric resistance member 19 is arranged, as shown in FIG. 4, at a location where it is less susceptible to heat from the exhaust gases, the O$_2$ sensor will always have sufficient internal resistance to avoid false detection of failure of the O$_2$ sensor and its wiring.

More advantageously, as shown in FIG. 10, the electric resistance member 19 may be arranged within the ECU 5 where it is further less susceptible to heat from the exhaust gases. Furthermore, according to this FIG. 10 arrangement, an ordinary type discrete fixed resistance sold on the market can be used as the electric resistance member 19 to enable reduction in the manufacturing cost.

FIG. 11 shows another arrangement of the O$_2$ sensor, which is distinguished from the FIG. 3 arrangement only in that there is provided a heater control unit 20, which may be controlled by the ECU 5. The heater control unit 20 has a heater resistance 21 arranged within the housing 15a of the O$_2$ sensor 15 to heat the O$_2$ sensor 15 with the electric resistance member 19 arranged within its housing 15a, in order to promote activation of the O$_2$ sensor and more stably control the temperature thereof.

FIG. 12 shows a further arrangement of the O$_2$ sensor, which is identical with the FIG. 10 arrangement except that it is provided with a heater control unit as used in FIG. 11, for the same purposes as the one in FIG. 11. As compared with an ordinary type discrete resistance forming the electric resistance member 19, the internal resistance 18b of the O$_2$ sensor 15 varies at a larger rate with change in its temperature. Therefore, preferably, depending upon the type of the engine, at least the O$_2$ sensor per se, i.e. the internal resistance 18b should be thermally controlled by the heater control unit 20.

The mounting location of the electric resistance member 19 is not limited to those illustrated, but it may be another place outside the ECU 5, insofar as it is not susceptible to heat from the exhaust gases.

What is claimed is:

1. A method of detecting failure of an exhaust gas component concentration sensor having a sensing element formed of one pair of electrodes between which a solid electrolytic member is interposed, for detecting concentration of a component of exhaust gases from an internal combustion engine, the air-fuel ratio of an air-fuel mixture supplied to said engine being controlled in a feedback manner responsive to a difference between an output voltage value from said sensor and a predetermined reference voltage value, the method comprising the steps of:

(1) connecting a voltage supply source to said one pair of electrodes of said sensor for applying a predetermined voltage thereto,
   (2) determining whether or not a change in said output voltage caused by said application of said predetermined voltage to said sensor is smaller than a predetermined value, and
   (3) detecting that said sensor is faulty when said change in said output voltage is smaller than said predetermined value.

2. A method according to claim 1, wherein it is decided that said sensor is faulty when said change in said output voltage caused by said application of said predetermined voltage to said sensor has continued to be smaller than said predetermined value over a predetermined time period.

3. A method according to claim 2, wherein it is decided that said sensor is faulty when said change in said output voltage caused by said application of said predetermined voltage to said sensor has continued to be smaller than said predetermined value over a first predetermined time period, and further continued to be smaller than said predetermined value over a second predetermined time period following said first predetermined time period.

4. A method according to claim 1, comprising the steps of determining whether or not said output voltage is within a predetermined value range which can be assumed during normal operation of said engine, storing a value of said output voltage when said output voltage first falls outside said predetermined value range, determining whether a second difference between said stored value of said output voltage and each of subsequent actual values of said output voltage is smaller than a predetermined value, applying said predetermined voltage to said sensor when said second difference has continued to be smaller than said predetermined value over a first predetermined time period, and deciding that said sensor is faulty when said second difference has continued to be smaller than said predetermined value over a second predetermined time period after said application of said predetermined voltage to said sensor.

5. A method according to claim 1, wherein said steps (1) to (3) are carried out during said feedback control.

6. A method according to claim 1, wherein said steps (1) to (3) are carried out after a predetermined time period has elapsed after said engine entered a predetermined feedback control region, when said feedback control is not being carried out.

7. A method according to claim 6, wherein said predetermined time period is equal to a time period required for activation of said sensor.

8. A method according to claim 6 or claim 7, wherein said predetermined time period is set to a shorter value as the engine temperature is higher.

9. In a device for sensing concentration of a component of exhaust gases from an internal combustion engine, including:
an exhaust gas component concentration sensor having a solid electrolytic element, and a pair of electrodes provided on said solid electrolytic element, one of said electrodes being exposed to a reference gas, and the other of said electrodes being exposed to said exhaust gases; and
electric current supply means for supplying a predetermined amount of electric current to said solid electrolytic element;
a voltage corresponding to the concentration of said exhaust gas component being developed between said electrodes when said predetermined amount of electric current is supplied to said solid electrolytic element from said electric current supply means;
the improvement comprising an electric resistance member connected in series between said electric current supply means and one of said electrodes for improving accuracy of detecting disconnection and short-circuit in said sensor.

10. A device according to claim 9, wherein said electric resistance member is connected in series between said electric current supply means and said one of said electrodes being exposed to said reference gas.

11. A device according to claim 9, wherein said electric resistance member is arranged within said sensor.

12. A device according to claim 9, wherein said electric resistance member is arranged outside said sensor.

13. A device according to claim 12, including an electronic control unit for controlling the air-fuel ratio of a mixture supplied to said engine in response to an output from said sensor, and wherein said electric resistance member is arranged within said electronic control unit.

14. A device according to any one of claims 11-13, including heater control means for heating said sensor.

15. A device for detecting failure of an exhaust gas component concentration sensing device, said sensing device including:
an exhaust gas component concentration sensor having a solid electrolytic element, and a pair of electrodes provided on said solid electrolytic element, one of said electrodes being exposed to a reference gas, and the other of said electrodes being exposed to said exhaust gases;
electric current supply means for supplying a predetermined amount of electric current to said solid electrolytic element;
said electric current supply means having a terminal connected to said one of said electrodes;
a voltage corresponding to the concentration of said exhaust gas component being developed between said electrodes when said predetermined amount of electric current is supplied to said solid electrolytic element from said electric current supply means; and
an electric resistance member connected in series between said electric current supply means and one of said electrodes;
the device comprising:
a constant voltage supply source for applying a predetermined voltage to said sensing device, and
a switch connected between said constant voltage supply source and said one of said electrodes for applying said predetermined voltage to said one of said electrodes when said switch is closed.

* * * * *